(12) United States Patent
Gelder et al.

(10) Patent No.: US 8,389,479 B2
(45) Date of Patent: Mar. 5, 2013

(54) COMPOSITIONS AND METHODS FOR TREATMENT OF MULTIPLE SCLEROSIS

(75) Inventors: Frank B. Gelder, Auckland (NZ); Gillian Alison Webster, Auckland (NZ)

(73) Assignee: Innate Immunotherapeutics Limited (NZ)

( * ) Notice: Subject to any disclaimer, the term of this patent is extended or adjusted under 35 U.S.C. 154(b) by 0 days.

(21) Appl. No.: 12/639,733

(22) Filed: Dec. 16, 2009

(65) Prior Publication Data

US 2010/0317589 A1    Dec. 16, 2010

(30) Foreign Application Priority Data

Jun. 16, 2009 (NZ) ........................ 577731

(51) Int. Cl.
*A61K 38/14* (2006.01)
*C07K 14/47* (2006.01)
(52) U.S. Cl. ...................... 514/17.9; 514/20.9
(58) Field of Classification Search .................. None
See application file for complete search history.

(56) References Cited

U.S. PATENT DOCUMENTS 6,335,017 B1 * 1/2002 Gelder ........................ 424/208.1
2010/0292153 A1 * 11/2010 Strober ........................ 514/16.6

FOREIGN PATENT DOCUMENTS

| WO | WO 2008/070564 A1 | 6/2008 |
| WO | WO 2008/150181 A1 | 12/2008 |
| WO | WO 2008/150182 A1 | 12/2008 |
| WO | WO 2008/123481 A1 | 10/2009 |

OTHER PUBLICATIONS

Liu G., et al., "Solid-phase synthesis of muramyl dipeptide (MDP) derivatives using a multipin method", Bioorganic and Medicinal Chemistry Letters, 2000, 10(3):1361-1363.
Ohya Y., et al., "Synthesis of MDP Analogue/Chitin Conjugate That Stimulates Cultured Macrophages". Journal of Bioactive and Compatible Polymers, 1993, 8: 351-364.
Root-Bernstein, R.S. et al. "Clinical Suppression of Experimental Allergic Encephalomyelitis by Muramyl Dipeptide "Adjuvant"" Brain Research Bulletin, 1986, 17(4):473-476.
Tabata, Y. et al. "Macrophage activation through phagocytosis of muramyl dipeptide encapsulated in gelatin microspheres", Journal of Pharmacy and Pharmacology, 1987, 39(9):698-704.
Schwartzman S.M., et al., "A Shortened Synthesis of Adjuvant Dipeptide", Prep Biochem, 1980, 10(3):255-267.

* cited by examiner

*Primary Examiner* — John Ulm
(74) *Attorney, Agent, or Firm* — Lisa M. Treannie, Esq.; Morse, Barnes-Brown & Pendleton, P.C.

(57) ABSTRACT

Disclosed are novel compositions and methods for the treatment of Multiple Sclerosis (MS), and in particular immunostimulatory compositions comprising muramyl dipeptide microparticles for use, e.g., in the treatment of MS.

12 Claims, 8 Drawing Sheets

COMPOSITIONS AND METHODS FOR TREATMENT OF MULTIPLE SCLEROSIS

RELATED APPLICATIONS

This application claims priority to New Zealand Application No.: 577731, filed on Jun. 16, 2009. The entire teachings of the above application are incorporated herein by reference.

TECHNICAL FIELD

The present invention is concerned with novel compositions and methods for the treatment of Multiple Sclerosis (MS) and in particular with immunostimulatory compositions comprising muramyl dipeptide microparticles in the treatment of MS.

BACKGROUND

Multiple sclerosis (abbreviated MS), is an autoimmune condition in which the immune system attacks the central nervous system, leading to demyelination. Disease onset usually occurs in young adults, and it is more common in females. It has a prevalence that ranges between 2 and 150 per 100,000.

MS affects the ability of nerve cells in the brain and spinal cord to communicate with each other. Nerve cells communicate by sending electrical signals called action potentials down long fibers called axons, which are wrapped in an insulating substance called myelin. In MS, the body's own immune system attacks and damages the myelin. When myelin is lost, the axons can no longer effectively conduct signals. The name multiple sclerosis refers to scars (scleroses—better known as plaques or lesions) in the white matter of the brain and spinal cord, which is mainly composed of myelin. Although much is known about the mechanisms involved in the disease process, the cause remains unknown. Theories include genetics and/or infections. Different environmental risk factors have also been found.

Almost any neurological symptom can appear with the disease, and often progresses to physical and cognitive disability. MS takes several forms, with new symptoms occurring either in discrete attacks (relapsing forms) or slowly accumulating over time (progressive forms). Between attacks, symptoms may go away completely, but permanent neurological problems often occur, especially as the disease advances. MS is sometimes incidentally identified during neurological examinations performed for other causes.

There is no known cure for MS. Treatments attempt to return function after an attack, prevent new attacks, and prevent disability. MS medications can have adverse effects or be poorly tolerated, and many patients pursue alternative treatments, despite the lack of supporting scientific study. The prognosis is difficult to predict; it depends on the subtype of the disease, the individual patient's disease characteristics, the initial symptoms and the degree of disability the person experiences as time advances.

The life expectancy of people with MS, at least for earlier years, is nearly the same as that of unaffected people. Almost 40% of patients reach the seventh decade of life. Nevertheless, half of the deaths in people with MS are directly related to the consequences of the disease, while 15% more are due to suicide, a percentage much higher than in the healthy population.

Although most patients lose the ability to walk prior to death, 90% are still capable of independent walking at 10 years from onset, and 75% at 15 years.

MS results in a thinning or complete loss of myelin and, as the disease advances, the cutting (transection) of the neuron's extensions or axons. When the myelin is lost, a neuron can no longer effectively conduct electrical signals. A repair process, called remyelination, takes place in early phases of the disease, but the oligodendrocytes cannot completely rebuild the cell's myelin sheath. Repeated attacks lead to successively fewer effective remyelinations, until a scar-like plaque is built up around the damaged axons.

Apart from demyelination, which is caused by T cells, the other pathologic hallmark of the disease is inflammation. The central involvement of a wide range of inflammatory mediators in progressive multiple sclerosis is well established. These factors play multiple roles including facilitating T cell migration into the central nervous system (CNS), break down of blood-brain barrier and promotion of myelin destruction and axon degeneration in the early phase of disease. The later phase is associated with predominantly neuroaxonial damage as a result naked axon exposure in demyelinated plaques.

Treatment

Although there is no known cure for multiple sclerosis, several therapies have proven helpful. The primary aims of therapy are returning function after an attack, preventing new attacks, and preventing disability. As with any medical treatment, medications used in the management of MS have several adverse effects. Alternative treatments are pursued by some patients, despite the shortage of supporting, comparable, replicated scientific study.

Current treatment strategies involve both immunomodulating as well as immunosuppressive strategies which are aimed at reducing the inflammatory phase. During symptomatic attacks, administration of high doses of intravenous corticosteroids, such as methylprednisolone, is the routine therapy for acute relapses. The aim of this kind of treatment is to end the attack sooner and leave fewer lasting deficits in the patient. Although generally effective in the short term for relieving symptoms, corticosteroid treatments do not appear to have a significant impact on long-term recovery. Potential side effects include osteoporosis and impaired memory, the latter being reversible.

Disease-modifying treatments are expensive and most of these require frequent (up-to-daily) injections. Others require IV infusions at 1-3 month intervals. Non-specific agents such as interferons have limited long term efficacy and are not well tolerated.

As of 2007, six disease-modifying treatments have been approved by regulatory agencies of different countries for MS. Three are interferons: two formulations of interferon beta-1a (trade names Avonex, CinnoVex, ReciGen and Rebif) and one of interferon beta-1b (U.S. trade name Betaseron, in Europe and Japan Betaferon). A fourth medication is glatiramer acetate (Copaxone). The fifth medication, mitoxantrone, is an immunosuppressant also used in cancer chemotherapy, approved only in the USA and largely for secondary progressive MS. The sixth is natalizumab (marketed as Tysabri), an anti-VLA-4 antibody which blocks immune cell trafficking and effectively reduce CNS inflammation. All six medications are modestly effective at decreasing the number of attacks and slowing progression to disability, although their efficacy rates differ, and studies of their long-term effects are still lacking. Comparisons between immunomodulators (all but mitoxantrone) show that the most effective is natalizumab, both in terms of relapse rate reduction and halting disability progression; it has also been shown to reduce the severity of MS. Mitoxantrone may be the most effective of them all; however, it is generally not considered as a long-term therapy, as its use is limited by severe cardiotoxicity.

The interferons and glatiramer acetate are delivered by frequent injections, varying from once-per-day for glatiramer acetate to once-per-week (but intra-muscular) for Avonex. Natalizumab and mitoxantrone are given by IV infusion at monthly intervals. Treatment of progressive MS is more difficult than relapsing-remitting MS. Mitoxantrone has shown positive effects in patients with secondary progressive and progressive relapsing courses. It is moderately effective in reducing the progression of the disease and the frequency of relapses in patients in short-term follow-up. No treatment has been proven to modify the course of primary progressive MS.

A number of treatments that may curtail attacks or improve function are under investigation. Some of these treatments involve the combination of drugs that are already in use for multiple sclerosis, such as the joint administration of mitoxantrone and glatiramer acetate (Copaxone). However, most treatments already in clinical trials involve drugs that are used in other diseases. Most recently, auto-antibodies reactive with neurofascin 186, a principle nerve fibre protein, have been strongly implicated in neuronal degeneration associated with progressive MS, and represent a potential new target.

As with any medical treatment, these treatments have several adverse effects. One of the most common is irritation at the injection site for glatiramer acetate and the interferon treatments. Over time, a visible dent at the injection site, due to the local destruction of fat tissue, known as lipoatrophy, may develop. Interferons produce symptoms similar to influenza; some patients taking glatiramer experience a post-injection reaction manifested by flushing, chest tightness, heart palpitations, breathlessness, and anxiety, which usually lasts less than thirty minutes. More dangerous are liver damage from interferons and mitoxantrone, the immunosuppressive effects and cardiac toxicity of the latter; and the putative link between natalizumab and some cases of life-threatening complications such as progressive multifocal leukoencephalopathy.

Therefore there is still a need for alternative MS treatments which have improved therapeutic and side-effect profiles.

It is an object of the present invention to overcome or ameliorate at least one of the disadvantages of the prior art therapies or provide a useful alternative.

SUMMARY OF THE INVENTION

According to a first aspect of the present invention there is provided a method of treating multiple sclerosis comprising the administration to a subject requiring such treatment of a composition comprising muramyl dipeptide cross-linked into a microparticle.

According to the present invention there is also provided a method of treating multiple sclerosis comprising administering to a subject requiring such treatment an effective amount of a composition comprising muramyl dipeptide cross-linked to form a microparticle. According to the present invention there is also provided a method of treating multiple sclerosis comprising administering to a subject requiring such treatment an effective amount of a composition comprising a microparticle comprising cross-linked muramyl dipeptide.

According to another aspect of the present invention there is provided a method of treating symptoms of multiple sclerosis comprising the administration to a subject requiring such treatment of a composition comprising muramyl dipeptide cross-linked into a microparticle.

According to a further aspect of the present invention there is provided a method of co-therapy in the treatment of multiple sclerosis comprising the administration to a subject requiring such treatment of a composition comprising muramyl dipeptide cross-linked into a microparticle and another active agent effective in the treatment of multiple sclerosis.

Preferably the type of multiple sclerosis to be treated is progressive multiple sclerosis. The progressive multiple sclerosis can be primary progressive, secondary progressive or chronic progressive multiple sclerosis. Alternatively, the type of multiple sclerosis to be treated is relapsing-remitting multiple sclerosis.

The compositions comprising muramyl dipeptide cross-linked into a microparticle (e.g., MIS416) may be administered to a subject by any known means but it is preferably administered by infusion or injection. Suitable modes of administration can also be chosen from intramuscular, intraperitoneal, intravenous, subcutaneous, rectal, nasal, oral, intragastric, pulmonary and the like.

The dose of MIS416 can be easily determined by a medical practitioner, taking into consideration the type of multiple sclerosis, severity of disease and its symptoms and overall condition of the patient. Typically the dose given will be in the range of 50 µg to 1500 µg and may be given daily, weekly, fortnightly or monthly. An example of a suitable dosage regimen could be to start with an initial dose of 100 µg of MIS416 followed by doses escalated by for example 50 µg-200 µg per week or fortnight, until appropriate beneficial therapeutic effects are observed in the patient, without significant side-effects. The dosage may be given as single bolus dose or infused over time, or given in divided doses.

When administered as a co-therapy, MIS416 may be administered with other active agents used in the treatment of MS, for example steroids, interferons, antibodies, and the like.

Other active agents used in the treatment of MS, which could be used in conjunction with MIS416 may be selected from corticosteroids, such as methylprednisolone, interferons, such as interferon beta-1a and interferon beta-1b, glatiramer acetate, mitoxantrone, antibodies, such as natalizumab, or combinations thereof.

MIS416 may be given concurrently with other agents effective in the treatment of MS, or may be given sequentially.

According to an additional aspect, the present invention provides muramyl dipeptide cross-linked into a microparticle or a composition comprising muramyl dipeptide cross-linked into a microparticle for the treatment of multiple sclerosis.

The present invention also provides muramyl dipeptide cross-linked to form a microparticle or a composition comprising muramyl dipeptide cross-linked to form a microparticle. The invention provides a microparticle comprising cross-linked muramyl dipeptide or a composition comprising a microparticle comprising cross-linked muramyl dipeptide.

According to a further aspect, the present invention provides muramyl dipeptide cross-linked into a microparticle or a composition comprising muramyl dipeptide cross-linked into a microparticle for the treatment of symptoms of multiple sclerosis. In one embodiment the composition comprises an amount of muramyl dipeptide cross-linked into a microparticle effective to treat symptoms of multiple sclerosis when administered in an appropriate treatment regimen.

According to an additional aspect, the present invention provides muramyl dipeptide cross-linked into a microparticle or a composition comprising muramyl dipeptide cross-linked into a microparticle for co-therapy in the treatment of multiple sclerosis.

In the context of the present invention, compositions comprising muramyl dipeptide cross-linked into a microparticle are referred to herein as MDP-microparticle compositions. One example of a formulation or preparation comprising an MDP-microparticle composition in sodium chloride is interchangeably referred to as MIS or MIS416, as described in the examples and shown in the figures.

DETAILED DESCRIPTION OF THE PREFERRED EMBODIMENT

Figure 1:
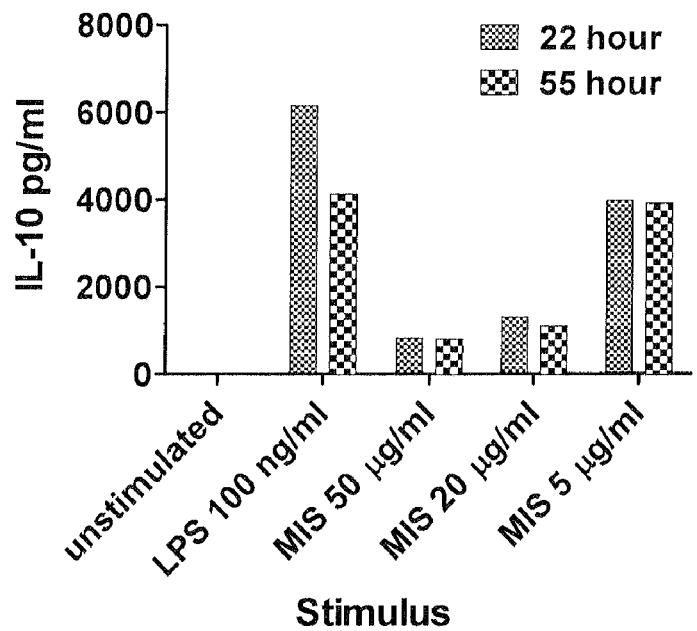
FIG. 1 illustrates that MIS416 induces anti-inflammatory cytokines.
Figure 1:
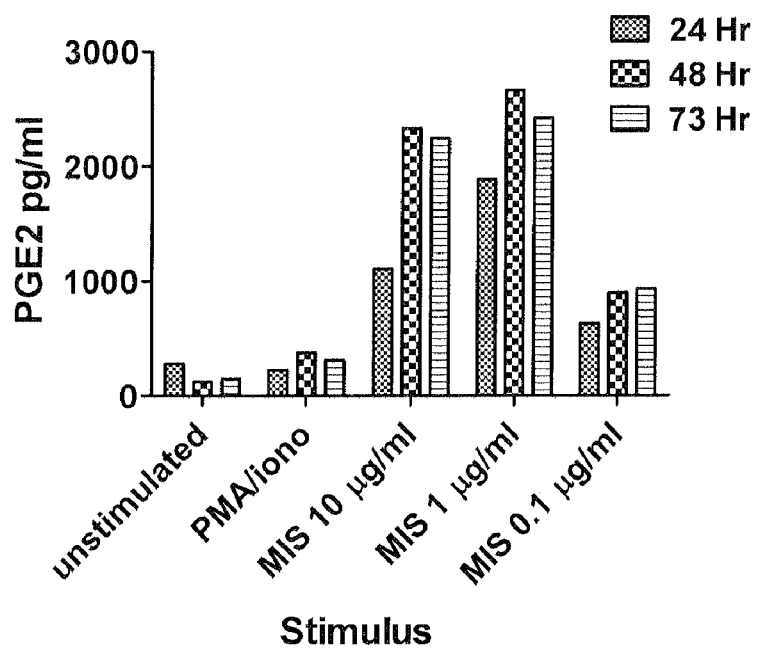

It has now been unexpectedly found that muramyl dipeptide in the form of a microparticle that comprises fragments of DNA, which can modulate several aspects of the immune system simultaneously, may represent a more effective treatment for MS, of both the progressive and relapsing-remitting type. Without wishing to be bound by any theory, the microparticle of the present invention appears to also contain DNA fragments which can modulate several aspects of the immune system simultaneously. As demonstrated herein by way of a case study of a patient with progressive MS and animal models of relapsing-remitting MS, multi-dose treatment with a composition comprising muramyl dipeptide cross-linked into a microparticle (MDP microparticle or MIS416), is efficacious as a stand-alone therapy, without causing significant side-effects.

MIS416 is a multi-modal immune response modifier which activates a wide range of immunoregulatory pathways implicated in the management of MS. These include the induction of natural anti-inflammatory mediators such as IL-10 and $PGE_2$, which also serve to inhibit de-regulated T and B cell responses MIS416 treatment of a progressive MS patient and animals with relapsing-remitting MS demonstrates reduction in serum levels of adhesion molecules important in leucocyte trafficking. In particular MIS416 is effective at reducing sVCAM-1, which interacts with the leukocyte integrin VLA-4. This suggests that MIS416 therapy downregulates MS associated-upregulation of these molecules. Therapeutic benefit from modulating this VLA-4 dependant trafficking pathway has been validated by Natalizumab, however MIS416 is non-toxic. MIS416 therapy also shows modulation of elevated levels of ICAM-1 and E-selectin.

In contrast to other approved agents for treatment MS, MIS416 is non-toxic and non-immunogenic, and is suitable for long term treatment MIS416-containing compositions may be administered by any suitable means. Exemplary methods of administration are intramuscular injection, subcutaneous injection, intravenous injection, intra peritoneal injection, eye drop, via drinking water, aerosol, or nasal spray. When administered to animals, any suitable veterinary formulation may be used. In addition to those described above, formulations may be in the form of powders or pastes and may be added to feed or administered orally in the usual manner. Suitable formulation protocols and excipients can be found in standard texts such as Remington: The Science and Practice of Pharmacy, $19^{th}$ Ed, 1995 (Mack Publishing Co. Pennsylvania, USA), British Pharmacopoeia, 2000, and the like.

The appropriate individual dosage of MDP microparticle composition, total amount administered and duration of administration can be easily determined by a medical practitioner based on guidance provided herein, the nature and severity of MS and its symptoms, and the response by the patient to the treatment. As an example, useful individual dosages may be selected from the range 50 μg to 1000 μg, and may be administered daily, weekly or monthly depending on patient's condition, symptoms, tolerance and response to treatment. The MDP microparticle composition can be administered at doses selected from about 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975 or 1000 μg. Doses in a higher range can also be used depending on the requirements, for examples doses in the range of 50 μg to 1500 μg. The total amount of MDP-microparticle administered will depend on patient response and tolerance to treatment. The composition may be administered daily, weekly, fortnightly or monthly for a total period that depends on the patient's response.

Without wishing to be bound by any particular mechanism of action, it is believed that action of MIS416 involves at least in part a transient inflammatory phase, a grade 1-3 fever and chills in association with a therapeutic dose. Thus, an initial dose of 50 μg to 100 μg of MIS416 could be expected to trigger little or no response and therefore may constitute an appropriate first dose in a dose escalation treatment regimen where the objective is to ultimately trigger a minor fever and chills response. In the absence of such a response, dosing could be escalated by, for example, 50 μg per week or fortnight until the patient reports the desired mild (Grade 1 to 2) fever and chills response. The dosing interval may vary depending on patient's response and tolerance to treatment and may involve more frequent dosing with smaller amounts of MDP-microparticle composition (eg. the weekly or fortnightly dose may be split into smaller doses and given daily, twice weekly or some other suitable interval). This can easily be determined by medical practitioners based on patient's response.

It will be clear to those skilled in the art that MIS416 treatment may form a component of co-therapy in the treatment of MS. Thus, MIS416 may be administered in conjunction with other known therapies for MS such as interferons, steroids, antibodies and the like. In co-therapy treatment MIS416 may be administered simultaneously or sequentially with other treatments.

The invention will now be described more particularly with reference to non-limiting examples.

EXAMPLES

Example 1

Preparation of MDP-Microparticle

A multiple repeat of muramyl dipeptide (MDP) isolated from *Propionibacterium acini*, formed the core structure of the MDP-microparticle immunostimulant of this example. The chemical composition of the preferred monomeric subunit is as shown below.

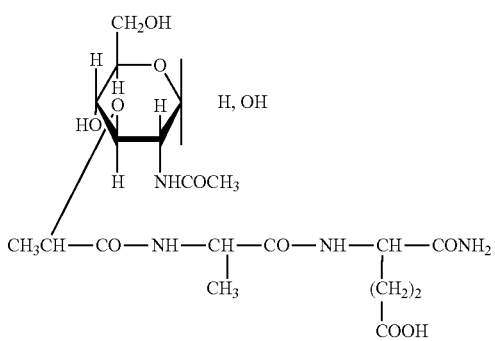

MDP has well known immunostimulatory properties, which have been extensively evaluated in studies designed to determine its effect on increasing immune function. To date, both MDP isolated from natural sources and synthetic MDP have been associated with significant toxicity when administered to mammals. This toxicity has limited the effectiveness of MDP as an adjuvant.

A method for the isolation of MDP, free from toxic components, is described in the co-pending international application PCT/NZ2009/000049, incorporated by reference herein. Briefly, *Propionibacterium acnes* was grown to a mid-stationary growth phase and washed to remove contaminants of bacterial culture origin employing techniques well known to those in the art. Hydrophobic components contained in the cell walls and cytoplasm were sequentially extracted by successive washes with increasing concentrations of ethanol/isopropanol/water (10%:10%:80%, 25%:25%:50% and 40%:40%:20%) at elevated temperatures. The isopropyl alcohol is then removed with successive washes with decreasing concentrations (80%, 50%, 40% and 20%) of ethanol at elevated temperatures. The resulting MDP-microparticle is then suspended in 6M guanidine-HCl and then washed into water for irrigation and its concentration measured by relating its absorbance at 540 nm to the absorbance of turbidity standards.

Analysis of this preparation demonstrated muramyl dipeptide extensively crosslinked and having a microparticle size predominantly in the range of 1 to 3 microns. The MDP-microparticles contain muramic acid with amino-linked L-alanine-D-isoglutamine dipeptide and bacterial DNA fragments. Thus, muramyl dipeptide cross-linked into a microparticle produced by processes described in co-pending international application PCT/NZ2009/000049, and uses thereof such as for therapy of MS, are within the scope of the described invention. Without wishing to be bound by any particular theory, it is believed that the DNA fragment(s) are likely to be a bioactive component of the microparticle. Such a microparticle can be isolated from natural sources, as above, or synthesized using well-known synthetic procedures (for example, Liu G.; Zhang S.-D.; Xia S.-Q.; Ding Z.-K. Bioorganic and Medicinal Chemistry Letters, 10 (12), 2000, pp. 1361-1363(3); Schwartzman S. M., Ribi E., Prep Biochem. 1980; 10(3): 255-67; Ohya et al. Journal of Bioactive and Compatible Polymers, 1993; 8: 351-364). The MDP microparticles generated by the present methods can have a broad range of sizes (for example, 0.01-30 microns) but the most common size range is from 1 to 7 microns. The preferred size is in the range of 0.5-3 microns.

The concentration of the MDP-microparticle was adjusted to 10 mg/mL sodium chloride for i.v. administration and dispensed into single dose vials containing 1.5 mL. This formulation of MDP-microparticle in sodium chloride is referred to herein as MIS or MIS416. It will be understood that MIS416 is used throughout as an exemplary embodiment only, and that disclosure relating to MIS416 is equally applicable to other MDP-microparticle formulations and compositions.

When a patient is receiving MIS416, it is preferable to pre dilute the MIS416 to a more convenient concentration for administration when administering doses less than 1000 μg (1 mg). This may be accomplished by withdrawing the appropriate volume of MIS416 from the drug vial using an insulin syringe and injecting the dose into a second syringe containing 1-2 mL of normal saline for injection.

Example 2

MIS416 Stimulation of Human PBMC Results in the Production of Anti-Inflammatory Cytokines IL-10 and PGE2

Human PBMC ($10^6$/mL) were cultured with LPS (*E coli*; 100 ng/mL) which served as an assay positive control or MIS416 at 50, 20 and 5 μg/mL for a total culture period of 55 hours. Cell-free supernatants were harvested at 22 hours and 55 hours and assayed for secreted IL-10 using flow cytometric cytokine bead array technology according to the manufacturers' standard protocols (Bender MedSystems GmbH, Vienna, Austria). Results are provided in FIG. 1.

Human PBMC ($10^6$/mL) were cultured for a total of 96 hours with MIS at 10, 1 and 0.1 μg/mL. PMA (1 nM)+ Ionomycin (100 ng/mL) co-stimulation served as an assay positive control. Cell-free supernatants were collected at 24, 48 and 72 hours and assayed for PGE2 using a commercial PGE2 ELISA used exactly according to manufacturers recommendation (R&D Systems Inc. Minneapolis, USA). Results are provided in FIG. 1.

Example 3

Figure 2:
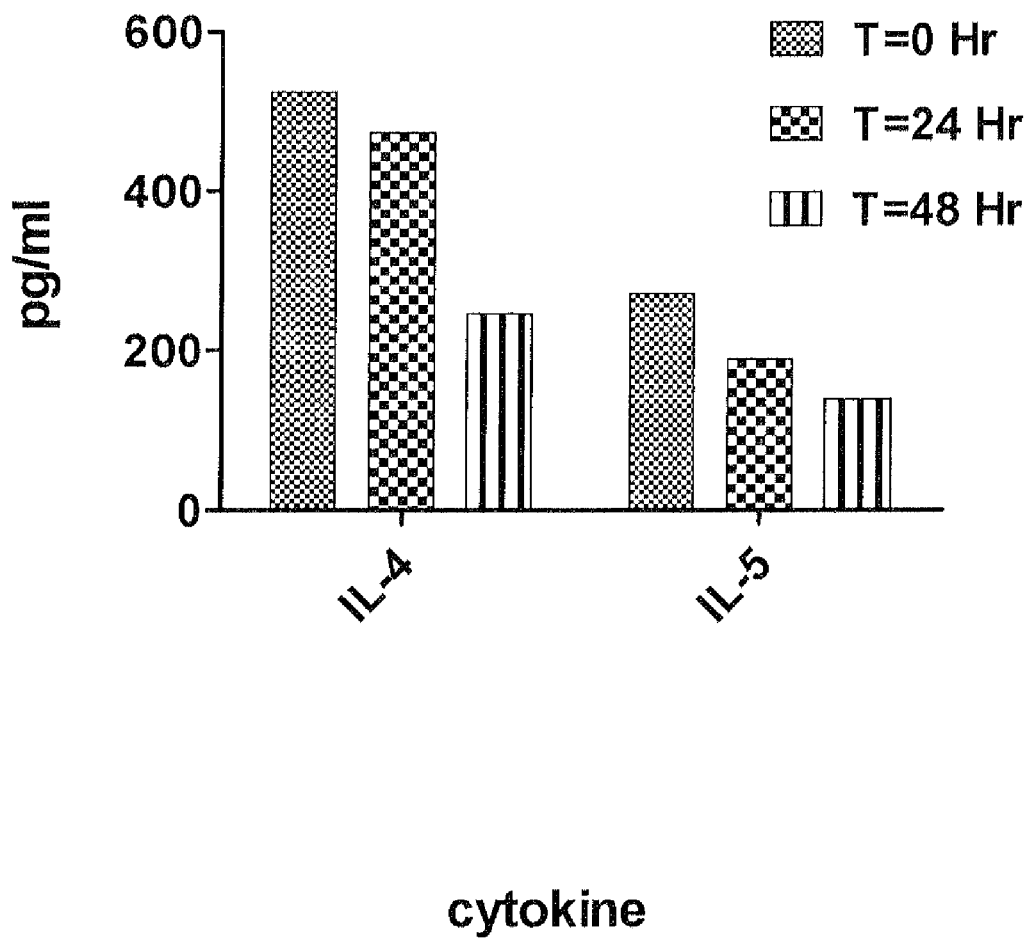
FIG. 2 shows inhibition of serum Th2 cytokines in MS patient following single i.v. bolus of MIS416.

MIS416 Therapy Reduces Serum Levels of Cytokines Known to be Involved in Humoral Immunity and Autoantibody Production Peripheral blood serum was harvested from a patient receiving a single dose of MIS416 under compassionate use immediately prior to, and at 24 and 48 hours following, a single i.v. bolus of MIS416 diluted in saline. IL-4 and IL-5 in the serum was determined using flow cytometry bead array technology according to manufacturer's instructions (Bender MedSystems GmbH, Vienna, Austria). Results are provided in FIG. 2.

Example 4

Figure 3:
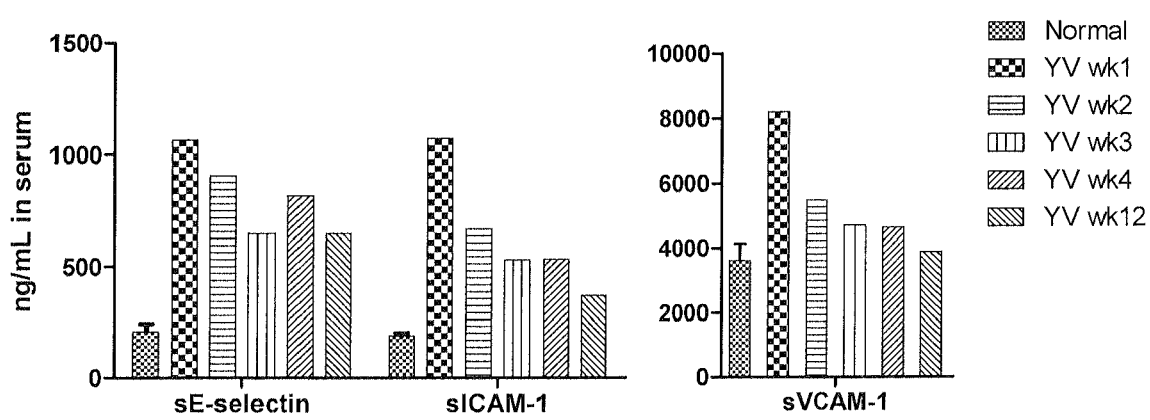
FIG. 3 shows that MIS416 therapy of a progressive MS patient for up to 12 weeks leads to reduced serum levels of cell-adhesion molecules important for leukocyte migration.

MIS416 Therapy Reduces Serum Levels of Cell Adhesion Molecules Central to Leukocyte Trafficking Heparin anti-coagulated peripheral blood from progressive multiple sclerosis patient YV was collected immediately prior to MIS416 dosing on weeks 1, 2, 3, 4 and 12 of MIS therapy. Serum was harvested from the blood and stored at −80° C. until analysis. Serum samples were analysed for soluble adhesion molecules sE-selectin, sICAM-1 and sVCAM-1 simultaneously using flow cytometric bead array technology (Bender MedSystems GmbH, Vienna, Austria). Results are provided in FIG. 3.

Example 5

MIS416 Therapy for the Treatment of Progressive Multiple Sclerosis Results in Inhibition of Disease Progression and Improvement in Existing Disease Symptoms and Quality of Life In New Zealand under the medicines act, a patient may receive a non-licensed medicine on a compassionate use basis. In the progressive multiple sclerosis patient example described below, MIS416 was administered as a stand alone therapy by single bolus i.v. "push" diluted in saline. The dose schedule received is detailed in Table 1. All doses of MIS416 were diluted to a final volume of 2 ml in saline.

TABLE 1

Dose regimen for the treatment of patient YV
Patient YV

| Dose # | Timing of Dose | Size of Dose (μg) |
|---|---|---|
| 1 | Day 1 | 1500 |
| 2 | Day 9 | 150 |
| 3 | Day 16 | 250 |
| 4 | Day 23 | 250 |
| 5 | Day 30 | 350 |
| 6 | Day 37 | 500 |
| 7 | Day 44 | 500 |
| 8 | Day 49 | 500 |
| 9 | Day 58 | 500 |
| 10 | Day 64 | 550 |
| 11 | Day 71 | 550 |
| 12 | Day 79 | 650 |
| 13 | Day 86 | 750 |
| 14 | Day 93 | 750 |
| 15 | Day 100 | 750 |
| 16 | Day 107 | 750 |
| 17 | Day 114 | 800 |
| 18 | Day 121 | 800 |
| 19 | Day 137 | 500 |
| 20 | Day 151 | 500 |
| 21 | Day 165 | 500 |
| 22 | Day 186 | 250 |
| 23 | Day 200 | 350 |
| 24 | Day 214 | 400 |

An MRI scan was performed after 6 doses to provide a basis for determining any subsequent changes in the rate and nature of progression or any other improvements that may be documented by MRI scanning techniques. The initial MRI scan showed brain and spinal cord lesions typical of long standing progressive MS. The patient had no sensation in, and has been unable to move, her legs and feet for over a year. Regular blood samples were taken to monitor the patient's CPCs (white blood counts, enzymes etc).

Notes on Progress of Treatment (i) Following the initial high dose (1500 μg) of the MIS416 composition the patient experienced some side effects which necessitated a re-evaluation of the dosage regimen for future weekly dosing with MIS416 in saline. An analgesic was to be administered at the time of giving the dose of MIS416, if required.

As to any other effects of the initial high dose treatment, on a follow-up one week after administration of the initial does of the MIS416 composition the patient was asked to wiggle her toes and discovered that she was actually able to accomplish this—for the first time in a year.

(ii) The second dose was administered at 100 μg of the MIS416 composition. The patient kept a detailed diary during the course of treatment.

(iii) Following the third dose of 250 μg of the MIS416 composition there were no appreciable side effects. The patient felt more sensation in the top of feet and can feel the bones of her feet and much better strength in her back and stomach (her torso). An old symptom had returned—the patient is now experiencing very painful heels at night in bed.

(iv) After her fourth dose of the MIS416 composition (350 μg), the patient suffered a bad headache on the same day but on the following day she was very well and could feel her knees. Further, she was now able to lift her arms above her head. The patient felt this is a huge step forward.

The patient also reported that her hands, which previously were purple and cold, were now warm and pink. She also lost the constant flushing in her face.

(vii) An out-of-town relative who has not seen the patient for about six months visited shortly after the seventh dose of treatment with MIS614, and was profoundly impressed with her physical and mental improvement. At that time the patient managed to stand on her feet for the first time for nearly a year! The patient says that her toes are constantly tingly and that she can feel the bones on top of her feet again. Circulation in patient's hands and feet was much better and both are now constantly pink and warm instead of purple and cold. The patient is also no longer constantly cold.

She regained sensation in her back and can now feel the backrest of her wheelchair against her back. The patient still has a depressed appetite and any previous food cravings have gone.

(viii) Following the eighth dose of MIS416 the patient was very excited to report that she had managed to sit up (from lying prone in the bed) all by herself, to her and her physiotherapist's surprise.

The patient continues to stand every day (supporting herself with only one crutch) and notes that she is standing much straighter. She still cannot take any steps but feels the standing is stronger. Burning sensation in her heels is still there— particularly in one foot.

The patient has also developed a sore back (because she can actually feel her back now which she could not do before). She can now stretch her legs in bed, which was not possible before, but is still unable to roll over in bed although she frequently tries to do so.

(ix) No major additional changes were reported following administration of ninth through eighteenth doses of MIS416, except that the sleep pattern had improved and that her appetite had come back but without particular food cravings. The patient continues to feel increased sensation in her feet and notes that she is beginning to feel good all the time, particularly the day after administration of a dose of treatment. Upper body strength continues to improve.

(x) Following the administration of the nineteenth does of MIS416 the treatment regimen was altered from a weekly to a fortnightly administration, to assist with further reduction of side effects such as headaches and leg tremors. Following the administration of the twentieth and twenty first dose the patient continues to feel well and the altered regimen appears to have alleviated the headaches. She is sleeping well and can still feel the harness she wears to bed (she has retained the sensation in her back). She is still able to hold herself up when she is being put to bed.

(xi) Following the last three doses of MIS416 the patient noticed further improvement in her feet: she is able to feel appropriate sensations in her feet such as hot and cold. Previously she felt numbness and nothing, then as feeling returned, the prickling, followed by burning heels and now she has whole foot sensation responsive to local conditions.

The patient feels that she is standing a little more strongly and is feeling better standing than before. Continues to feel strengthening in her upper body. She can dry her own hair now because she has strength enough to raise her arms. She can do the dishes "without falling into the sink". She still has some weakness in the upper body but it is much improved.

The patient reported that the difficulty she had with focusing with one of her eyes before MIS treatment appears to have been resolved since the first dose of MIS, and the eye now focuses normally.

The patient feels very positive and is sure that she is slowly improving.

TABLE 2

A summary of the improvements following MIS416 treatment

| Before MIS416 treatment | After MIS416 treatment |
| --- | --- |
| Unable to weight-bear on legs | Able to stand (assisted) for up to one minute and doing so several times per day, every day.<br>Three weeks after completion of treatment stood up three times over the day for two minutes at a time.<br>Husband notes the patient is much easier to lift as she seems to have more strength to help get up<br>The patient is standing straighter than before |
| Upper body unable to support itself in wheelchair | Upper body strength improved by 80% |
| Slumping to right side and falling forward during meals and at kitchen tasks | Never slumps to right side anymore<br>Requesting that back support in wheelchair be removed - not required.<br>No longer requires wheelchair headrest except when traveling in vehicle. |
| Would slump forwards at mealtimes and at the dishwasher | 100% better. Never falls forward at mealtimes or at dishwasher |
| No sensation in back.<br>Unable to feel clothes, back of wheelchair or harness used on the hoist | 80% of sensation has returned. |
| Spasms or tremors in legs at night in bed, sometimes of five minutes' duration a number of times during the night | Only very occasionally on a much reduced scale (intensity of tremors reduced by 50%) and only near the end of the fortnightly MIS dose time |
| Flushing in face in afternoons continuing on until nightfall | Almost completely disappeared - happens occasionally near the end of the fortnightly MIS dose time |
| Feet very painful, burning pains "as if feet were going to burn off" | Burning pains completely gone. |
| Unable to feel external temperature in feet | Feet now respond appropriately to external temperature (ie feet cold when air temperature is cold) |
| Feet - complete lack of any kind of sensation in feet | Able to feel pain appropriately when feet are bumped, stood on or pulled. |
| Feet - unable to move at all in any way | 50% improvement. Able to wiggle all toes. Still no strength in feet but has movement and sensation. |
| Legs - inability to move | Able to bring knees together |
| When lying flat in bed is unable to lift legs at all or move legs in any way | Able to flex thigh muscles<br>Strength in thigh muscles is increasing |
| Pelvic area - unable to move in any way | Able to "wiggle" posterior to adjust her position in the bed and to help with dressing or to adjust her position in her wheelchair<br>Can now "flex my hip so I can feel the muscles"<br>Able to wriggle into position for the hoist which lifts her off the bed |
| Lymphoedema in legs and feet<br>Wears support hose for this | Noticeable lessening in fluid retention.<br>Husband notes it is easier to put the support hose on her feet. |
| Hands - no strength to hold even a cigarette or pencil between fingers. | Holding a pen and writing has improved by about 50%. |

TABLE 2-continued

A summary of the improvements following MIS416 treatment

| Before MIS416 treatment | After MIS416 treatment |
|---|---|
| Completely unable to sew any more. | Three weeks after completion of treatment: Handwrote her diary for two hours with no problems. Spent three hours typing the diary on the computer with no tiredness or problems. |
| Hands - Unable to cut own meat at mealtimes | Still has not enough strength to manage this although can hold the knife and fork |
| Hands - unable to complete small movements like buttoning own clothes, buckling a belt, tying a bow | 10% improvement with buttons. Can buckle a belt. |
| Hands - unable to complete fine movements tasks in dressing like zips or buttons if she cannot see them (eg behind back) | 10% improvement in being able to do this |
| Hands - weak. Unable to do baking and difficulty cooking as cannot transfer heavy pots from stove to bench or lift. Unable to stir cake mixtures etc | 80% improvement though still needs help with heavier items. Notes that while the forearms and hands are still weak, the shoulders and biceps are stronger |
| Hands - weak. Unable to turn taps on to handwash clothes | Can now stretch and reach over and has enough strength to turn on the taps. Left arm has become painful from overuse as has not got full strength yet. |
| Hands\Arms - Weak. Unable to dress herself as could not even pull her shirt over her head. Could not lift arms above head at all. | Can now not only pull her own clothes on but can pull them over her head as well. |
| Arms weak. Unable to brush, wash or blowdry own hair | Can now do this unassisted. |
| Facial Neuralgia - Daily dose of 200 mls of Tegretol taken for last five years Would experience "really really painful" sudden attacks of pain in various parts of the face "like someone hammering a nail into your face" | Tegretol has been stopped two weeks after conclusion of treatment with MIS416. One fleeting incident experienced for a few seconds five days after stopping Tegretol |
| Dysphagia - Over the last two years has intermittently experienced problems swallowing - "the food just won't go down". Physio advised to lower chin which seems to help | 80% improvement |
| Swallowing - An intermittent problem laughing and swallowing concurrently - or breathing and laughing concurrently | Improvement |
| Eyesight - difficulty focusing. < afternoons. One eye would not focus and would have to tilt head to one side to see someone in front of her | 100% improvement one week after first dose of MIS416 |
| Strength General - Feeling of being a "lump of meat, unable to move" | Husband notes that she is now of considerable help when getting her into the harness to hoist her out of bed. She can move her body into the harness better and can move extremities more easily. |
| Bowels slow. No sensation. Can be constipated for up to two weeks and not feel the urge to pass stool. | Much improved sensation. Can now feel the urge to pass stool and can feel the passing of stool itself, although still constipated and needs to take a mild laxative. |
| Energy. Would sometimes need to sleep at 11.00 am and again in the afternoon | Noticeable improvement. Never needs to sleep in the daytime. |

A follow up MRI scan was performed 6 months after initiation of therapy. It was noted that the extensive MS lesions documented in the previous scan were stable with no further lesions identified.

Example 6

Figure 4:
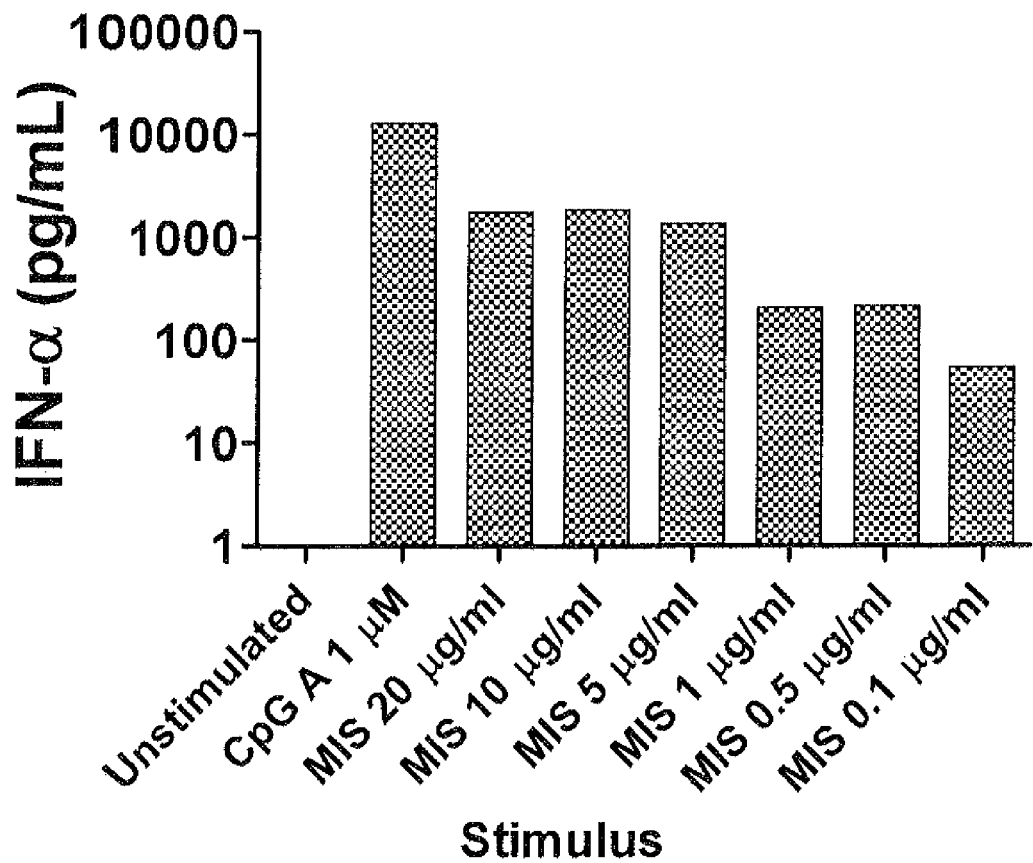
FIG. 4 illustrates that MIS416 induces IFNα production by plasmocytoid dendritic cells, the most potent IFNα secreting immune cell. IFNα has clinical utility in some forms of multiple sclerosis.

Induction of Immunoregulatory Type I Interferon by Plasmocytoid Dendritic Cells Following In Vitro Stimulation with MDP-Microparticle Human pDCs, potent INF-α producing cells were purified from PBMCs using magnetic bead selection of BDCA-2+ cells. Sorted cells ($10^6$/ml) were cultured (complete medium+5% Ab serum) with MDP microparticle or TLR9 type A ligand as an assay positive control. Culture supernatants were assayed for IFNα content using flow cytometry cytokine bead array methodology. The results shown in FIG. 4 demonstrate pDC dose-responsive induction of IFNα, a cytokine that offers therapeutic benefit for some types of multiple sclerosis.

Example 7

Figure 5:
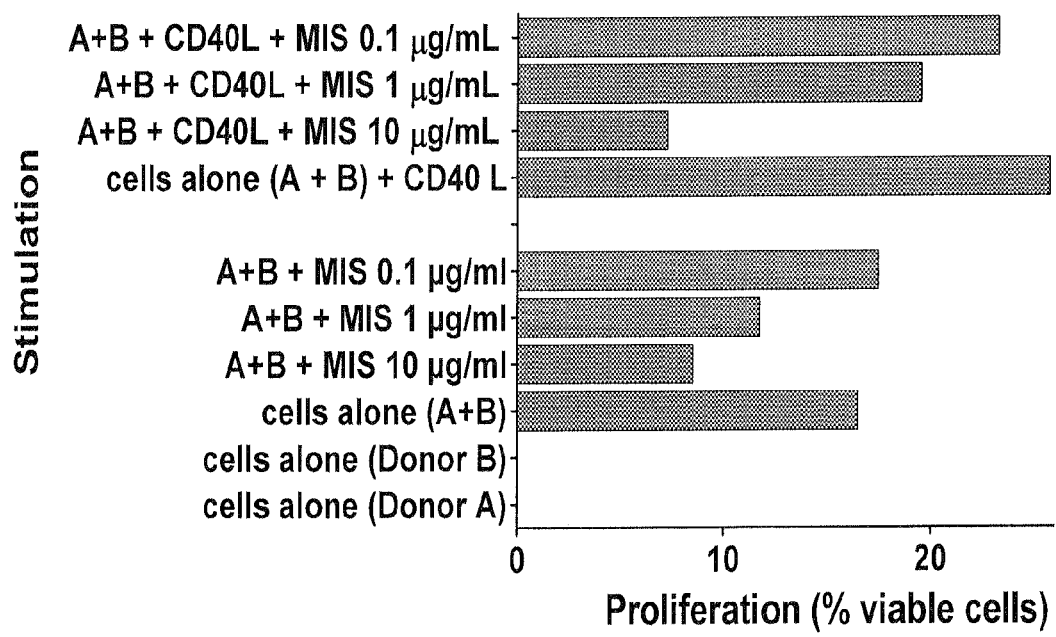
FIG. 5 shows that MIS416 inhibits T cell proliferation in response to non-self MHC antigen (allo antigen). Agents that can inhibit T cell proliferation have potential for reducing autoreactive T cell activation associated with multiple sclerosis.

Inhibition of Allo-Antigen-Induced T Cell Proliferation by MDP-Microparticle Co-Culture To simulate antigen-induced T cell proliferation, a 2 way mixed lymphocyte reaction was established. PBMC from two MHC I and MHC II mis-matched donors were obtained. One cohort (responder) was labeled with a cell division fluorescent indicator dye called CFSE dye (Invitrogen, USA), whilst the other cohort remained unlabelled (stimulator). Equal cell numbers of stimulators and responders were co-cultured in the presence of MDP microparticle at 10, 1 and 0.1 µg/mL with or without soluble CD40L, a known T cell co-stimulation factor for 5 days. Cells were labeled with viability dye (propidium iodide; Invitrogen, USA) and fluorescent antibodies reactive with CD3 cells (Sigma-Aldrich NZ Ltd, Auckland, New Zealand). Cells were analyzed by flow cytometry and live responder T cells were identified based on CFSE/CD3 fluorescence. The % that had divided, as indicated by reduced CFSE fluorescence compared to non-proliferating controls, was determined. As shown in FIG. 5, MDP microparticle inhibited alloantigen-induced T cell proliferation in the absence and presence of T cell co-stimulation factors. This indicates that MDP microparticle may also be able to modulate auto-antigen-induced T cell proliferation associated with multiple sclerosis.

Example 8

Figure 6:
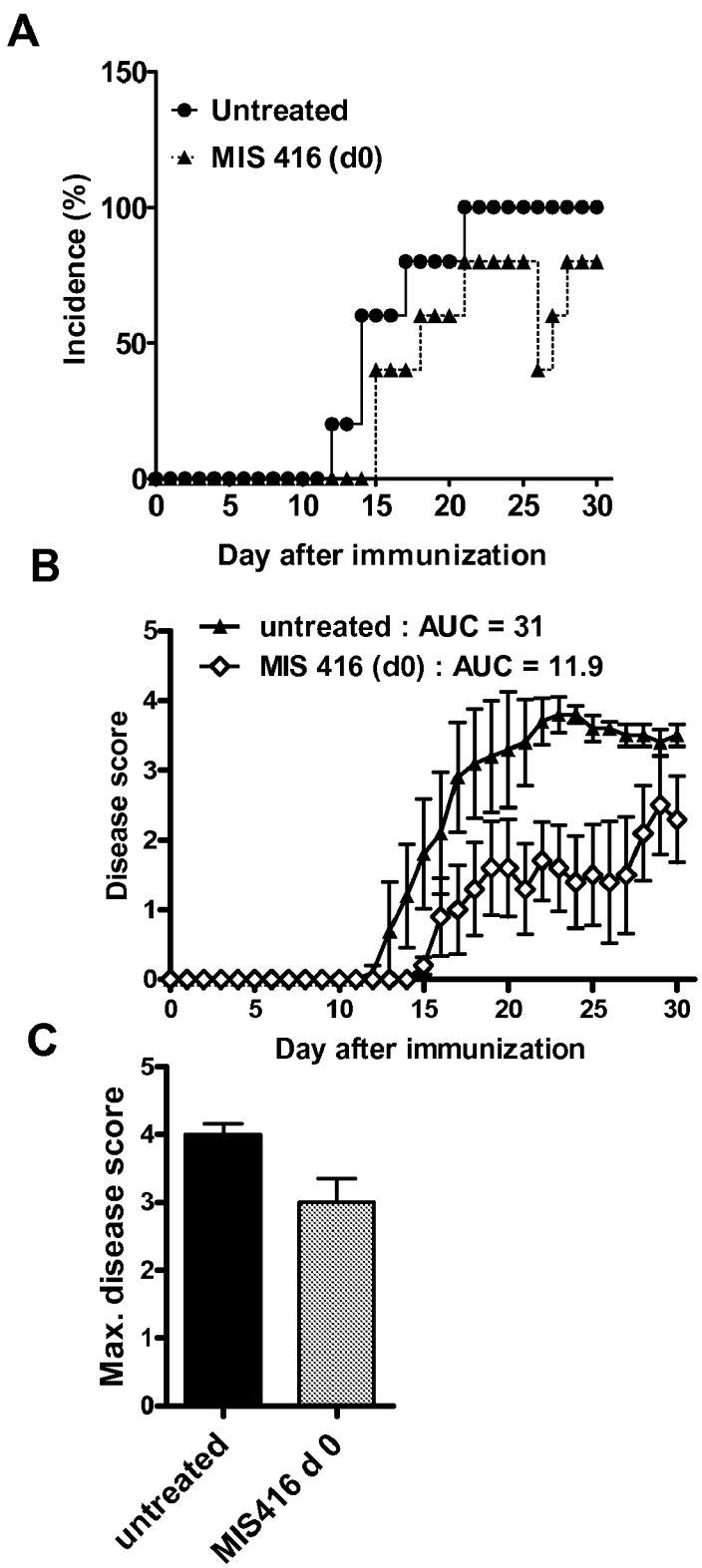
FIGS. 6A-6C show that MIS416 induces mechanisms that delay the rate of onset and incidence in a mouse model of relapse-remitting multiple sclerosis when administered at the time of disease induction.

MDP-Microparticle Treatment at the Time of Disease Induction Delays the Rate of Disease Onset and Incidence in the Murine Model of Relapsing-Remitting Multiple Sclerosis Mice (n=5) were immunized subcutaneously (s.c.) with myelin oligodendrocyte glycoprotein (MOG) peptide (Sigma-Aldrich NZ Ltd, Auckland, New Zealand) and Freund's adjuvant followed by pertusis toxin on day 2, intraperitonealy (i.p.). MDP microparticle (250 µg) was administered intravenously (i.v.) at the same time as the MOG+Freund's adjuvant immunization. The rate of experimental allergic encephalomyelitis (EAE) onset (FIG. 6A) and disease scores were measured (FIG. 6B). Disease scores were used to calculate the disease burden (area under the curve; AUC; FIG. 6B) and maximum disease score (FIG. 6C). These results demonstrate that administration of MDP microparticle i.v. at the time of immunization with MOG peptide in Freund's adjuvant s.c followed by pertusis toxin i.p on day 2 delays the onset and reduces the incidence of disease. AUC determinations as an indication of the total disease burden or "suffering" show that untreated animals have a value of 31, which is reduced to 11.9 for MDP microparticle treated animals. The maximum disease score is also significantly reduced in the treated group.

Example 9

Figure 7:
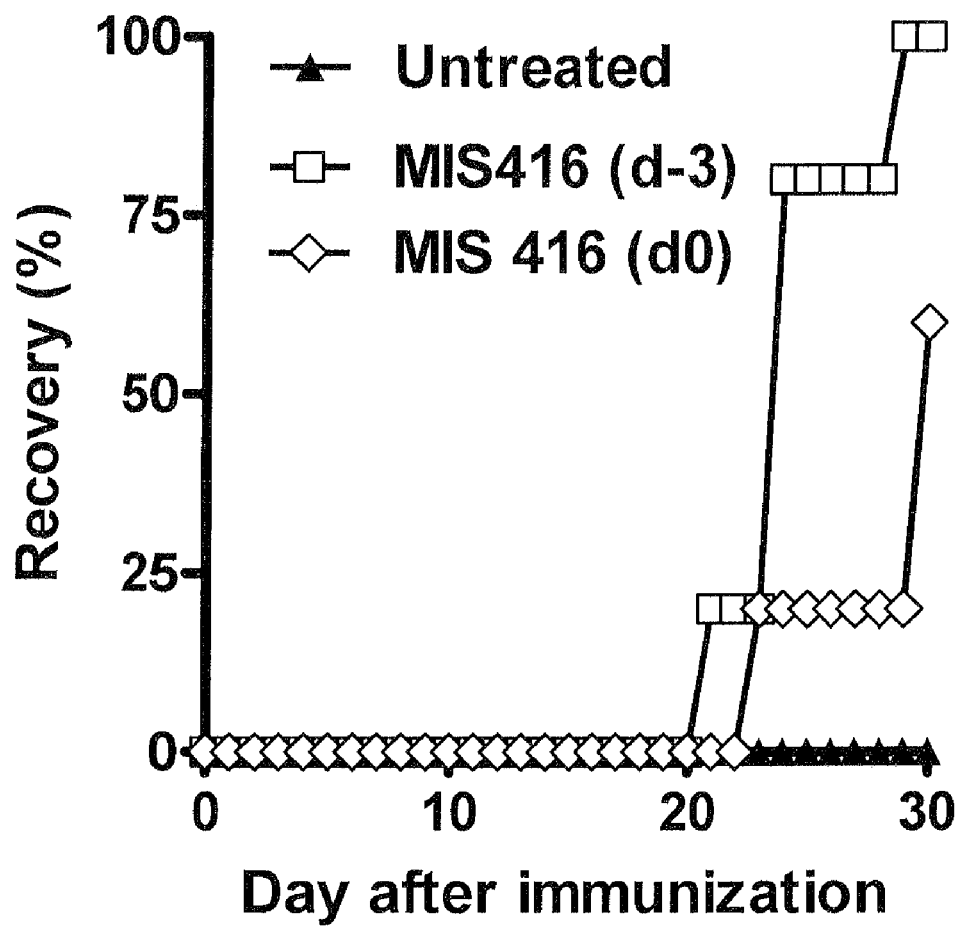
FIG. 7 illustrates that pre-treatment with MIS416 induces mechanisms that enhance the spontaneous recovery phase of disease in a relapse-remitting mouse model of multiple sclerosis.

MDP-Microparticle Treatment Prior to Induction of EAE Enhances the Spontaneous Recovery Phase in the Murine Model of Relapse-Remitting Multiple Sclerosis Mice (n=5) were treated with 250 µg MDP microparticle i.v. 3 days prior to EAE induction in a relapse-remitting model as described in Example 8, and the disease score was determined. Recovery was defined as day on which there was a >1.0 decrease from peak score occurred and was sustained. As shown in FIG. 7, pre-treatment with MDP microparticle showed a significant increase in the rate of onset of the spontaneous recovery phase compared to untreated mice, which showed no recovery over the time period examined. These results indicate that MDP microparticle therapy has the ability to modulate the severity or limit symptoms of multiple sclerosis associated with ongoing, active disease.

Example 10

Figure 8:
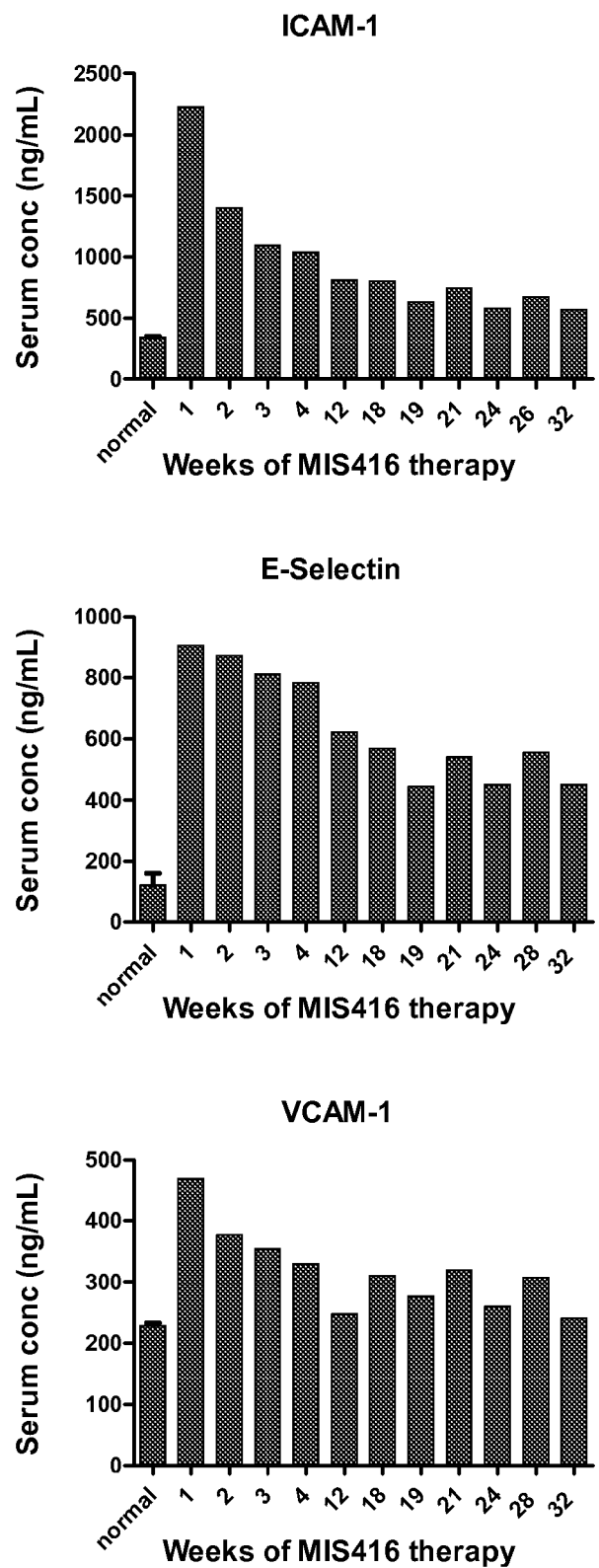
FIG. 8 demonstrates that long term MIS416 therapy in progressive MS patients leads to sustained reduction in elevated levels of soluble adhesion molecules important in leucocyte trafficking.

Long Term MDP Microparticle (MIS416) Therapy Sustains Reduced Serum Levels of Cell Adhesion Molecules Central to Leukocyte Trafficking Patient YV samples were obtained as described in Example 4 and encompassed ongoing MIS416 therapy up to week 32. Samples encompassing week 1 out to week 32 were evaluated to determine if the decreased levels of soluble adhesion molecules sE-selectin, sICAM-1 and sVCAM-1 detected by week 12 were sustained on MIS416 therapy. Serum samples were analysed for soluble adhesion molecules sE-selectin, sICAM-1 and sVCAM-1 simultaneously using flowcytometric bead array technology (Bender MedSystems GmbH, Vienna, Austria). Results are provided in FIG. 8. These results show that long term MIS416 therapy of 32 weeks leads to a sustained reduction in previously elevated levels of leucocyte trafficking molecules.

Although the invention has been described with reference to preferred embodiments and certain examples, it will be understood that variations and modifications in keeping with the thrust and spirit of the invention described herein are also contemplated and fall within the scope of the present invention.

We claim:
1. A method of treating multiple sclerosis comprising administering to a subject requiring such treatment a composition comprising muramyl dipeptide cross-linked into a microparticle.
2. A method of treating symptoms of multiple sclerosis comprising administering to a subject requiring such treatment a composition comprising muramyl dipeptide cross-linked into a microparticle.

3. A method according to claim 1, further comprising administering one or more other active agents effective in the treatment of multiple sclerosis.

4. A method according to any one of claims 1 to 3, wherein the type of multiple sclerosis to be treated is selected from progressive and relapsing-remitting multiple sclerosis.

5. A method according claim 4, wherein the progressive multiple sclerosis is selected from primary progressive, secondary progressive or chronic progressive multiple sclerosis.

6. A method according to claim 4, wherein the type of multiple sclerosis to be treated is relapsing-remitting multiple sclerosis.

7. A method according to any one of claims 1 to 3, wherein the composition is administered by means selected from intramuscular, intraperitoneal, intravenous, subcutaneous, rectal, nasal, oral, intragastric and pulmonary.

8. A method according to any one of claims 1 to 3, wherein the composition is administered by infusion or injection.

9. A method according to any one of claims 1 to 3, wherein the composition is administered in dose range of from 50 µg to 1500 µg.

10. A method according to any one of claims 1 to 3, wherein the composition is administered daily, weekly, fortnightly or monthly.

11. A method according to claim 3, wherein the one or more other active agents used in the treatment of multiple sclerosis is administered concurrently or sequentially, in any order, with the composition comprising muramyl dipeptide cross-linked into a microparticle.

12. A method according to claim 11, wherein the one or more other active agents used in the treatment of multiple sclerosis is selected from corticosteroids, interferons, glatiramer acetate, mitoxantrone, antibodies, or combinations thereof.

* * * * *